US008658804B2

(12) United States Patent
Jaensch

(10) Patent No.: US 8,658,804 B2
(45) Date of Patent: Feb. 25, 2014

(54) PROCESS FOR PREPARING N-SUBSTITUTED CYCLIC IMIDES

(75) Inventor: Helge Jaensch, Brussels (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 115 days.

(21) Appl. No.: 13/202,128

(22) PCT Filed: Feb. 1, 2010

(86) PCT No.: PCT/US2010/022727

§ 371 (c)(1), (2), (4) Date: Sep. 13, 2011

(87) PCT Pub. No.: WO2010/120398

PCT Pub. Date: Oct. 21, 2010

(65) Prior Publication Data

US 2011/0319635 A1 Dec. 29, 2011

Related U.S. Application Data

(60) Provisional application No. 61/165,714, filed on Apr. 1, 2009.

(30) Foreign Application Priority Data

May 8, 2009 (EP) .................................... 09159820

(51) Int. Cl.
*C07D 209/48* (2006.01)

(52) U.S. Cl.
USPC .......................................................... 548/473

(58) Field of Classification Search
USPC .......................................................... 548/473
See application file for complete search history.

(56) References Cited

U.S. PATENT DOCUMENTS

| | | | |
|---|---|---|---|
| 4,954,639 | A | 9/1990 | Fertel et al. |
| 7,368,615 | B2 | 5/2008 | Ishii et al. |
| 2006/0229196 | A1 | 10/2006 | Ishii et al. |
| 2006/0281629 | A1 | 12/2006 | Ishii et al. |

FOREIGN PATENT DOCUMENTS

| | | |
|---|---|---|
| CN | 1051170 | 5/1991 |
| JP | 2001-233854 | 8/2001 |
| JP | 2002-047270 | 2/2002 |
| JP | 2002-128760 | 5/2002 |
| JP | 2003-081941 | 3/2003 |
| JP | 2004-051626 | 2/2004 |
| WO | 95/25090 | 9/1995 |

OTHER PUBLICATIONS

Ishida, et al. Document No. 138:256906 retrieved from STN, CAPLUS; Mar. 19, 2003.*

Agrawal, *"Dissociation Constants of Some Hydroxamic Acids"*, Zeitschrift fuer Naturforschung, 1976, vol. 31B, No. 5, pp. 605-606.

Benjamin et al., *"The Synthesis of Unsubstituted Cyclic Imides Using Hydroxylamine Under Microwave Irradiation"*, Molecules, 2008, vol. 13, pp. 157-169.

Edafiogho et al., *"Synthesis and Anticonvulsant Activity of Imidooxy Derivatives"*, Journal of Med. Chemistry, 1991, vol. 34, pp. 387-392.

Einhorn et al., *"Mild and Convenient One Pot Synthesis of N-Hydroxyimides From N-Unsubstituted Imides"*, Synthetic Communications, 2001, vol. 31, No. 5, pp. 741-748. (No Translation).

Gross et al., *"Zur Darstellung Von N-Hydroxyphthalimid Und N-Hydroxyuccinimid"*, Journal fur praktische Chemie, 1969, vol. 311, pp. 692-693. (Abstract).

Imai et al., *"The Reaction of N-(Mesyloxy)Phthalimide and N-(Mesyloxy)Succinimide With Various Amines"*, Nippon Kagaku Kaishi, 1975, vol. 12, pp. 2154-2160.

Karakurt et al., *"Synthesis of Some 1-(2-Naphthyl)2-(Imidazole-1-yl)_Ethanone Oxime and Oxime Ether Derivatives and Their Anticonvulsant and Antimicrobial Activities"*, European Journal of Medical Chemistry, 2001, vol. 36, pp. 421-433.

Khan, *"Effect of Hydroxylamine Buffers on Apparent Equilibrium Constant for Reversible Conversion of N-Hydroxyphthalimide to o-(N-Hydroxycarbamoyl)-Benzohydroxamic Acid: Evidence for Occurrence of General Acid-Base Catalysis"*, Indian Journal of Chemistry, 1991, vol. 30A, pp. 777-783.

Sugamoto et al., *"Microwave-Assisted Synthesis of N-Hydroxyphthalimide Derivatives"*, Synthetic Communications, 2005, vol. 35, pp. 67-70.

* cited by examiner

*Primary Examiner* — Shawquia Young

(74) *Attorney, Agent, or Firm* — Jamie L. Sullivan; Siwen Chen

(57) ABSTRACT

In a process for making an N-substituted phthalimide compound, an amine is contacted with a carboxylic acid anhydride and allowed to react in an aqueous solution at a pH of about 2 to about 6. Optionally, the reactants are combined with an acid to lower the pH of the reaction solution wherein the lowering of the pH optimizes the yield of the desired N-substituted phthalimide product. The N-substituted phthalimide may be, for example, N-hydroxyphthalimide, and the reactants may be phthalic anhydride and hydroxylamine or a salt thereof. The N-substituted phthalimide compound is useful for, among other things, the oxidation of various hydrocarbons.

19 Claims, No Drawings

PROCESS FOR PREPARING N-SUBSTITUTED CYCLIC IMIDES

PRIORITY CLAIM

This application is a National Stage Application of International Application No. PCT/US2010/022727 filed Feb. 1, 2010, which claims priority to U.S. Provisional Application Ser. No. 61/165,714 filed Apr. 1, 2009, both of which are hereby incorporated by reference in their entirety.

FIELD

The present invention relates to a process for synthesizing N-substituted cyclic imides and, in particular, a process for synthesizing N-hydroxyphthalimide.

BACKGROUND

The oxidation of hydrocarbons is an important reaction in industrial organic chemistry. Thus, for example, the oxidation of cyclohexane is used commercially to produce cyclohexanol and cyclohexanone, which are important precursors in the production of nylon, whereas oxidation of alkylaromatic hydrocarbons is used to produce phenol, a precursor in the production of polycarbonates and epoxy resins.

N-substituted cyclic imides are useful as radical mediators in a number of radical based oxidation reactions. Specifically, the use of N-substituted phthalimides often allows for improved reaction rates, selectivities, and/or yields. Certain N-substituted phthalimides, particularly N-hydroxyphthalimide, are a good catalyst candidate for the oxidation of secondary butylbenzene (SBB) and cyclohexylbenzene (CHB) to their corresponding peroxides. SBB peroxide is an intermediate in the production of phenol and MEK, and CHB peroxide is an intermediate in the production of phenol and cyclohexanone.

Oxidation of hydrocarbons can be conducted using well-known oxidizing agents, such as $KMnO_4$, $CrO_3$ and $HNO_3$. However, these oxidizing agents have the disadvantage that their use is accompanied by the production of unwanted side products that can pose disposal and pollution problems. Preferably, therefore, oxidizing agents based on peroxides or $N_2O$ are used. The cheapest oxidizing agent, however, is molecular oxygen, either in pure form, or as atmospheric oxygen, or in dilute form. Oxygen itself is usually unsuitable for oxidizing hydrocarbons, however, since the reactivity of the $O_2$ molecule, which occurs in the energetically favorable triplet form, is not sufficient.

N-substituted cyclic imides useful in the oxidation of hydrocarbons suffer from the disadvantage that they are not currently available in large scale commercial quantities. As such, there are no large scale processes for the manufacture of N-substituted cyclic imides.

In accordance with the present invention, an optimized method of producing certain N-substituted cyclic imides is proposed in which N-substituted cyclic imides can be obtained in acceptable yields.

SUMMARY

In one aspect, the present invention resides in a process for making N-substituted cyclic imides, the process comprising:

a. a cyclic carboxylic acid anhydride with a hydroxylamine or a salt thereof in an aqueous solution to form a first mixture wherein the pH of the first mixture is from about 2 to about 6 and wherein the molar ratio of hydroxylamine to carboxylic acid anhydride in the first mixture is from about 0.8 to about 2.0 prior to reaction; and b. allowing the mixture to undergo reaction such that a N-substituted cyclic imide compound is formed.

Conveniently, the process may further comprise:

a. adding an acid to the first mixture to lower the pH of the first mixture to form a second mixture; and b. removing at least a portion of the N-substituted cyclic imide compound from the second mixture.

Conveniently, the process may even further comprise:

a. adding additional acid to the second mixture to further lower the pH of the second mixture; and b. removing at least a portion of the N-substituted cyclic imide compound.

DETAILED DESCRIPTION OF THE EMBODIMENTS

A "deprotonating base" means a base which reacts with a hydroxylamine salt to produce sufficient hydroxylamine to react with the cyclic carboxylic acid anhydride. Non-limiting examples of deprotonating bases to be used in the synthesis of N-Substituted cyclic imides are NaOH, $Na_2CO_3$, and $NH_3$. An "aqueous solution" means any liquid or slurry containing water.

The present invention provides a process for manufacturing a N-substituted cyclic imide. The process comprises contacting a cyclic carboxylic acid anhydride with a hydroxylamine N-substituted cyclic imide synthesis conditions have been identified that allow for reproducible formation of high purity a N-substituted cyclic imide in high yield from an aqueous solution of hydroxylamine or salt thereof (e.g. hydroxylamine sulfate and hydroxylamine hydrochloride) and cyclic carboxylic acid anhydride.

It is preferable to use a hydroxylamine salt such as hydroxylamine sulfate and hydroxylamine hydrochloride. Free hydroxylamine can be used, but free hydroxylamine may be difficult and dangerous to handle than hydroxylamine salts. Nevertheless, BASF currently does make a free hydroxylamine that can be used in the process of this invention called Hydroxylamine Free Base™ (50% aqueous solution).

Cyclic anhydrides which can be used in the process of this invention comprise the anhydrides of alicyclic, aromatic or heterocyclic dibasic carboxylic acids. Suitable acid anhydrides include, but are not limited to, 1,2,4,5-benzenetetracarboxylic acid anhydride, 1,2,4-benzene-tricarboxylic anhydride, 3,3',4,4'-benzophenonetetracarboxylic dianhydride, phthalic anhydride, 4-methylphthalic anhydride, tetrabromophthalic anhydride and tetrachlorophthalic, anhydride tetraphenyl phthalic anhydride, 3-nitrophthalic anhydride, cis-1,2,3,6-tetrahydrophthalic anhydride, and the like. Preferably, cyclic anhydrides which can be used in the process of this invention include phthalic anhydride and substituted phthalic anhydrides.

In one embodiment, phthalic anhydride is reacted with hydroxylamine to form N-hydroxyphtalimide (herein "NHPI"). NHPI synthesis is reproduced below. The reaction rates in the NHPI synthesis favor the production of NHPI when phthalic anhydride is added to an aqueous hydroxylamine solution as set forth below. It is undesirable to drive the reaction through the phthalic acid pathway (i.e. $k_2$) as the reaction rate constants $k_2$ and $k_3$ do not favor this pathway to form NHPI.

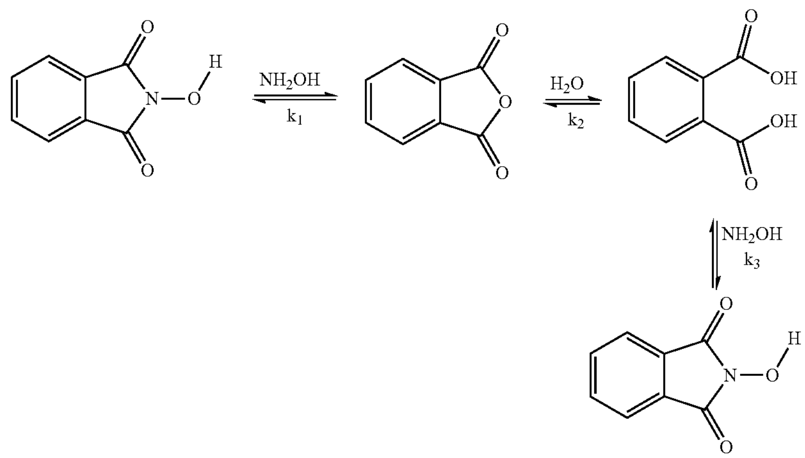

N-substituted cyclic imide compounds may be produced by contacting a cyclic carboxylic acid anhydride with a hydroxylamine or a salt thereof in an aqueous solution to form a first mixture. For example, the N-substituted cyclic imide compound can be NHPI, the cyclic carboxylic acid anhydride can be phthalic anhydride, and the hydroxylamine can be a hydroxylamine salt.

When using a hydroxylamine salt, it is preferable to deprotonate the hydroxylamine salt with a deprotonating base to form a hydroxylamine mixture. It is preferable for the hydroxylamine mixture to have a pH of from about 3 to about 10, from about 4 to about 9, from about 5 to about 8, from about 6 to about 8, or from about 6 to about 7.

For the case of synthesizing NHPI, reactor rates and yields are highest when starting from fully deprotonated hydroxylamine in aqueous solutions. Increasing hydroxylamine concentration and providing an excess of hydroxylamine may lead to increased yield. For example, a 1.5 fold excess of hydroxylamine (See Example 2) may lead to higher product purity.

The molar ratio of hydroxylamine to the cyclic carboxylic acid anhydride prior to reaction may be from about 0.8 to about 2.0, about 1 to about 1.8, about 1 to about 1.6, about 1 to about 1.5, about 1.1 to about 1.4, about 1.2 to about 1.3. It is preferable that the ratio of hydroxylamine to cyclic carboxylic acid anhydride be greater than 1.0.

Preferably the pH of the first mixture is from about 2 to about 10, about 2 to about 8, about 3 to about 7, about 2 to about 6, about 3 to about 6, about 4 to about 6, or about 5 to about 6. The first mixture may be allowed to undergo reaction such that an N-substituted cyclic imide compound is formed such as NHPI wherein all of the reaction, substantially all of the reaction, a majority of the reaction, or at least a portion of the reaction occurs at a temperature of less than about 100° C., or less than about 90° C., or less than about 80° C., or less than about 70° C. "Substantially all of the reaction" means that more about 90% of the reaction occurs at a given temperature such as a temperature of less than about 100° C., or less than about 90° C., or less than about 80° C., or less than about 70° C.

Recovery of N-substituted phthalimide is dependent on final pH. For example, a pH between about 1 to about 2 allows for maximum NHPI recovery with minimized NHPI decomposition. If the pH drops lower than about 1, then NHPI may decompose to phthalic acid which is undesirable.

Accordingly, a supplementary acid may be added to the first mixture to lower the pH of the first mixture to form a second mixture. Optionally, at least a portion of the N-substituted cyclic imide compound may be removed from the first mixture prior to the addition of the acid. It is preferable to use sulfuric acid or hydrochloric acid or other conventional acid that can be added to lower the pH of the solution without directly participating in the reaction. The pH of the second mixture may be less than about 7, less than about 6, less than about 5, less than about 4, less than about 3, less than about 2, or less than about 1. In another embodiment, the pH of the second mixture may be from about 1 to about 7, from about 1 to about 4, from about 1 to about 3, from 1 to about 2, from about 2 to about 6, or from about 3 to about 6.

After addition of the acid to the first mixture to form the second mixture, the desired product is allowed to precipitate in the second mixture. In one embodiment, the first mixture may be heated to a temperature of less than about 100° C. In another embodiment, the temperature of the first mixture may be less than about 90° C., less than about 80° C., or less than about 70° C. In still another embodiment, the temperature of the reaction may be from about 100° C. to about 90° C., about 90° C. to about 80° C., about 80° C. to about 70° C. The pH of the second mixture may be lowered to less than about 7, less than about 6, less than about 5, less than about 4, less than about 3, or less than about 2.

Optionally, the lowering of the pH of the first mixture can happen in a series of steps wherein (i) acid is added to the first mixture to form a second mixture, (ii) at least a portion of N-substituted cyclic imide is removed, (iii) acid is added to the second mixture after removal of the N-substituted cyclic imide to lower the pH of the second mixture, (iv) at least a portion of N-substituted cyclic imide is removed from the second mixture, (v) additional acid is added to the second mixture; (vi) at least a portion of N-substituted cyclic imide is removed from the second mixture; and so on. At the end of each acid addition step, the pH of the second mixture may be lowered to less than about 7, less than about 6, less than about 5, less than about 4, less than about 3, less than about 2, or less than about 1. In this embodiment, the temperature of the reaction may be less than about 90° C., less than about 80° C., or less than about 70° C. Additionally, the temperature of the reaction may be from about 100° C. to about 90° C., about 90° C. to about 80° C., about 80° C. to about 70° C.

Additionally, the synthesis of NHPI from hydroxylamine salts (hydroxylamine sulfate and hydroxylamine hydrochloride) and phthalic anhydride has been demonstrated in an alcohol (e.g. 2-butanol and methanol), or a biphasic medium comprising an alcohol and water (e.g. 2-butanol/water). The sequence utilizing methanol and hydroxylamine hydrochloride allows for monophasic reaction conditions and facilitates removal of inorganic salts formed during the reaction. The use of biphasic conditions allows for simple removal of organic products.

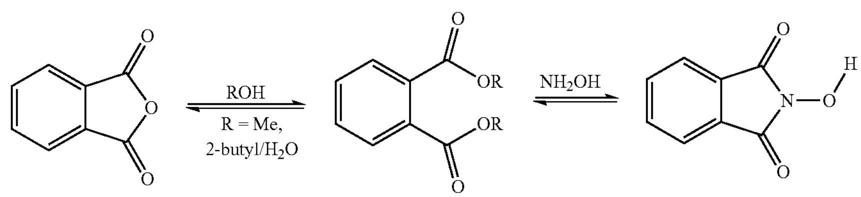

The catalyst prepared by this invention may be used for oxidizing a hydrocarbon to the corresponding hydroperoxide, alcohol, ketone, carboxylic acid or dicarboxylic acid. The oxidation process comprises contacting a reaction medium comprising a hydrocarbon feed with an oxygen-containing gas in a reaction zone and in the presence of a catalyst comprising a cyclic imide prepared by the method of the present invention. The hydrocarbon feed and general method of oxidation is described below.

Hydrocarbon Feed

Using the N-substituted cyclic imide prepared by the disclosed process a wide group of substituted or unsubstituted saturated or unsaturated hydrocarbons, such as alkanes, cycloalkanes, alkenes, cycloalkenes, and aromatics, can be selectively oxidized. In particular, however, the process has utility in the selective oxidation of isobutene to tertiary butyl hydroperoxide and tertiary butanol, the selective oxidation of cyclohexane to cyclohexanol and cyclohexanone and the selective oxidation of alkylaromatic compounds of the general formula (II) to the corresponding hydroperoxides:

(II)

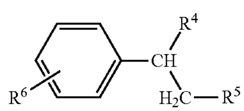

in which $R^4$ and $R^5$ each independently represents hydrogen or an alkyl group having from 1 to 4 carbon atoms, provided that $R^4$ and $R^5$ may be joined to form a cyclic group having from 4 to 10 carbon atoms, said cyclic group being optionally substituted, and $R^6$ represents hydrogen, one or more alkyl groups having from 1 to 4 carbon atoms or a cyclohexyl group. In an embodiment, $R^4$ and $R^5$ are joined to form a cyclic group having from 4 to 10 carbon atoms, conveniently a cyclohexyl group, substituted with one or more alkyl group having from 1 to 4 carbon atoms or with one or more phenyl groups. Examples of suitable alkylaromatic compounds are ethyl benzene, cumene, sec-butylbenzene, sec-penty-lbenzene, p-methyl-sec-butylbenzene, 1,4-diphenylcyclohexane, sec-hexylbenzene, and cycloh-exylbenzene, with sec-butylbenzene and cyclohexylbenzene being preferred. It will also be understood that in the case where $R^4$ and $R^5$ are joined to form a cyclic group, the number of carbons forming the cyclic ring is from 4 to 10. However, that ring may itself carry one or more substituents, such as one or more alkyl groups having from 1 to 4 carbon atoms or one or more phenyl groups, as in the case of 1,4-diphenylcyclohexane.

In one practical embodiment, the alkylaromatic compound of general formula (II) is sec-butylbenzene and is produced by alkylating benzene with at least $C_4$ alkylating agent under alkylation conditions and in the presence of a heterogeneous catalyst, such as zeolite beta or more preferably at least one molecular sieve of the MCM-22 family (as defined below).

In a further practical embodiment, the alkylaromatic compound of general formula (II) is cyclohexylbenzene and is produced by contacting benzene with hydrogen in the presence of a heterogeneous bifunctional catalyst which comprises at least one metal having hydrogenation activity, typically selected from the group consisting of palladium, ruthenium, nickel and cobalt, and a crystalline inorganic oxide material having alkylation activity, typically at least one molecular sieve of the MCM-22 family (as defined below).

Hydrocarbon Oxidation

The terms "group", "radical", and "substituent" are used interchangeably in this document. For purposes of this disclosure, "hydrocarbyl radical" is defined to be a radical, which contains hydrogen atoms and up to 20 carbon atoms and which may be linear, branched, or cyclic, and when cyclic, aromatic or non-aromatic. "Substituted hydrocarbyl radicals" are radicals in which at least one hydrogen atom in a hydrocarbyl radical has been substituted with at least one functional group or where at least one non-hydrocarbon atom or group has been inserted within the hydrocarbyl radical.

The oxidation step in the present process is effected by contacting the hydrocarbon substrate with an oxygen-containing gas in a reaction zone and in the presence of the N-substituted cyclic imide catalyst.

Generally, the cyclic imide that may be employed as the oxidation catalyst obeys the general formula:

(III)

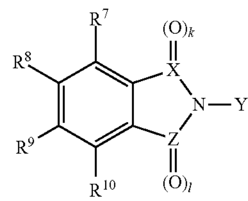

wherein each of $R^7$, $R^8$, $R^9$, and $R^{10}$ is independently selected from hydrocarbyl and substituted hydrocarbyl radicals having 1 to 20 carbon atoms, or the groups $SO_3H$, $NH_2$, OH and $NO_2$, or the atoms H, F, Cl, Br and I; each of X and Z is independently selected from C, S, $CH_2$, N, P and elements of Group 4 of the Periodic Table; Y is O or OH; k is 0, 1, or 2, and l is 0, 1, or 2. Conveniently, each of $R^7$, $R^8$, $R^9$, and $R^{10}$ is independently selected from aliphatic alkoxy or aromatic alkoxy radicals, carboxyl radicals, alkoxy-carbonyl radicals and hydrocarbon radicals, each of which radicals has 1 to 20 carbon atoms.

The desired product from the process of the present invention would fall under the cyclic imide of the general formula above. Accordingly, various cyclic carboxylic acids, including but not limited to phthalic anhydride, may be used as an intermediate along with hydroxylamine or a salt thereof to obtain the cyclic imide of above general formula.

In one practical embodiment, the cyclic imide catalyst comprises N-hydroxyphthalimide (NHPI) and is preferably present in the reaction zone in an amount between about 0.0001 wt % and about 5 wt %, such as between about 0.1 wt % and about 1 wt %, of the hydrocarbon substrate.

The oxidation of the hydrocarbon substrate is typically conducted at a temperature between about 20° C. and about 300° C., more particularly between about 50° C. and about 130° C. and/or a pressure between about 100 kPa and about 7000 kPa, more particularly greater than 500 kPa to about 5000 kPa and/or an oxygen concentration from 0.1 to 100% volume %, generally from about 2 to about 10 volume %, oxygen in the oxygen-containing gas.

Oxidation Product

The product of the present oxidation process depends on the nature of the hydrocarbon substrate being oxidized but in general is a hydroperoxide, alcohol, ketone, carboxylic acid or dicarboxylic acid, especially a hydroperoxide.

Where the hydrocarbon substrate is an alkylaromatic compound of the general formula (II), the product of the oxidation reaction includes a hydroperoxide of general formula (IV):

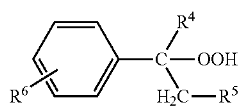

(IV)

in which $R^4$, $R^5$ and $R^6$ have the same meaning as in formula (II). Preferably, the hydroperoxide is sec-butylbenzene hydroperoxide or cyclohexylbenzene hydroperoxide. This hydroperoxide can then be converted by acid cleavage to phenol or a substituted phenol and an aldehyde or ketone of the general formula $R^4COCH_2R^5$ (V), in which $R^4$ and $R^5$ have the same meaning as in formula (II).

In one embodiment, the alkylaromatic compound that is oxidized is cyclohexylbenzene, the oxidation product is cyclohexylbenzene hydroperoxide, and the cleavage product comprises phenol and cyclohexanone. The crude cyclohexanone and crude phenol from the cleavage step may be subjected to further purification to produce purified cyclohexanone and phenol. A suitable purification process includes, but is not limited to, a series of distillation towers to separate the cyclohexanone and phenol from other species. The crude or purified cyclohexanone may itself be subjected to hydrogenation in order to convert it to phenol. Such hydrogenation may be performed, for example, over a catalyst such as platinum, nickel or palladium.

The invention will now be more particularly described with reference to the following non-limiting Examples.

The hydroxylamine sulfate, the phthalic anhydride, and the N-hydroxyphthalimide that was used in the following non-limiting Examples were supplied from Sigma-Aldrich Company.

Example 1

Invention

Dissolved 6.7 grams (40.9 mmole; 1.25 eq.) hydroxylamine sulfate $[(NH_2OH)_2SO_4]$ in 13.4 mL deionized water and slowly added 4.3 mL of 50 wt % (81.8 mmole) NaOH in 7.3 mL water to deprotonate the hydroxylamine sulfate. Added 10.9 grams (73.6 mmole) phthalic anhydride flakes to react with the hydroxylamine to form a mixture. Accordingly, the molar ratio of hydroxylamine to phthalic anhydride was approximately 1.25. After addition of phthalic anhydride started heating the mixture to 90° C. Mixture turned cloudy after 9 minutes (67° C.); phthalic anhydride not fully dissolved at this point. Added 25 mL DI water once mixture turned cloudy. Continued to heat and kept mixture at 90° C. for 15 minutes. Stopped heating and stirring after total of 30 minutes reaction time. Allowed to cool to room temperature. Filtered off white solids after 16 hours and dried for 3 hours at 75° C. Mother liquor pH at about 4-5.

First filtration yielded 8.9 grams N-hydroxyphthalimde (NHPI) at 98% purity. This translated into about a 72% yield.

Added 1 mL 30 vol % (6.2 mmole) H2SO4 to mother liquor until pH dropped to 2. No precipitation. Heated slightly to 75° C. for 5 minutes, then allowed to cool to room temperature. Formation of needles after 24 hours. Filtered off solids and dried solids for 3 hours at 75° C.

Second filtration yielded an additional 1.1 grams of NHPI at 98% purity which translates into about an additional 9% yield.

After filtration further precipitation from mother liquor at room temperature. Filtered off needles and “blobby” crystals.

Third filtration yielded at additional 0.3 grams of NHPI; however, the purity of this NHPI was only at about 62%.

Example 2

Invention

Dissolved 9.84 grams (60 mmole; 1.5 eq) hydroxylamine sulfate (HAS) in solution of 54 mL deionized water. Slowly added 6.3 mL 50 wt % NaOH solution. No gas evolution was observed. Added 11.84 grams (80 mmole) phthalic anhydride (PA) flakes. Accordingly, the molar ratio of hydroxylamine to phthalic anhydride is 1.5. After addition started heating to 90° C. PA dissolved completely and rapidly (pH=3-4). At 80° C. orange mixture turns turbid after 10 minutes. Shut down heating after 15 minutes at 90° C. Mother liquor at pH of about 6-7. Allowed to cool to room temperature. Filtered off yellowish solids after 1 hour and dried for 3 hours at 75° C. Mother liquor at pH of about 6.

First filtration yielded 6.64 grams of NHPI at 100% purity for a yield of approximately 50.9%.

Slowly added dilute (30 vol %) H2SO4 to mother liquor:

(i) 1 mL H2SO4 addition lowers pH to about 4 and solution turns less orange and more turbid.

(ii) 1 mL H2SO4 further addition lowers pH to about 3 and increased temperature of mother liquor to about 90° C. Suspension becomes thicker.

(iii) 1 mL H2SO4 further addition lowers pH to about 2 to 3. Suspension turns very clear (white) and allowed to cool to room temperature. Filtered off white solids and dried for 3 hours at 75° C.

Additional addition of 3 mL of H2SO4 yielded an additional 5.04 grams of NHPI at 100% purity.

Total solids recovery of 11.68 grams for a total yield of approximately 89.7%.

Example 3

NHPI Synthesis in 2-Butanol

Added 20 mL of 2-butanol to 3.07 grams (18.3 mmole) hydroxylammonium sulfate (HAS) in three necked flask equipped with reflux condenser and stir bar and heated to 100° C. No dissolution of HAS was observed. 5.42 grams (36.6 mmole) phthalic anhydride (PA) were added and the temperature increased to 120° C. (boiling point). PA dissolved completely, HAS only partially. Dispersion turned yellowish. Continued to vigorously stir at 120° C. HAS still not completely dissolved. Added approximately 0.5 mL deionized water to facilitate mass transport and continued to stir at reflux for a total of 3.5 hours. Removed yellow organic phase and filtered out white needles to form a first organic fraction. Evaporated solvent from mother liquor to obtain a second organic fraction. Added 2-butanol to white crystals and heated to reflux, but crystals do not dissolve. Added approximately 4 mL deionized water to 2-butanol/white crystal suspension to form a solvent fraction, whereupon white crystals dissolved at approximately 120° C. Formation of clear crystals in aqueous phase upon cooling of suspension. All fractions dried in N2 ventilated oven.

Recovered 1.14 grams of solids in first organic fraction said solids comprising 78% NHPI, 18 ester, and 3% phthalic acid.

Recovered 5.17 grams of solids in second organic fraction said solids comprising 5% NHPI, 77% ester, and 18% phthalic acid.

Recovered 1.00 grams of solids in solvent fraction comprising no NHPI, ester, or phthalic acid.

Example 4

NHPI Synthesis in Methanol

Added 5.42 grams (36.6 mmole) phthalic anhydride (PA) to 15 mL methanol and increased temperature to approximately 80° C. until solids dissolved. Added 2.55 grams (36.7 mmole) NH2OH(HCl) and continued to stir until hydroxylamine hydrochloride [NH2OH(HCl)] dissolved. No reaction visible at this point. Added 1.9 grams (18.3 mmole) Na2CO3 and witnessed evolution of CO2. Continued to stir for a total of 3 hours. Shut down heating and allowed to cool to room temperature. Evaporated off solvent, but only obtained yellow oil with dispersed white solids. Added 20 mL deionized water whereupon oil dissolves completely. No precipitation of solids over night at pH of approximately 6 to 7. Added concentrated sulfuric acid ($H_2SO_4$) dropwise. At entry point of acid formation of solids occurred that slowly dissolve in aqueous phase. Added acid until pH reached approximately 3 to 4 and precipitate does not dissolve anymore. Increased temperature to 80° C. for 10 minutes whereupon solids dissolve. Allowed to cool to room temperature. Filtered solids (fine needles) and dried for 3 hours at 75° C.

First filtration yielded 0.93 grams of precipitate (96% NHPI and 4% phthalic acid).

Removed solvent from mother liquor and tried to recrystallize by adding 30 mL deionized water. Solids do not fully dissolve. Allowed to cool to room temperature. Filtered solids (fine needles) and dried for 3 hours at 75° C.

Second filtration yielded 2.72 grams of precipitate (86% NHPI, 14% ester).

Example 5

NHPI Synthesis Under Biphasic Conditions

Added 10 mL 2-butanol to 5.42 grams (36.6 mmole) phthalic anhydride (PA) in three necked flask equipped with reflux condenser and stir bar and heated to 75° C. Added 2 mL of deionized water and increased temperature to 105° C. PA not fully dissolved. Added 5 mL of 2-butanol and increased temperature till reached the boiling point. After addition of 1 mL of deionized water a clear solution forms (i.e. no aqueous phase visible). Slowly added 3.07 grams hydroxylammonium sulfate (HAS). After addition completed, second phase present. Solution turns slightly yellow after approximately 1 hour. Stirred at reflux for total of 4 hours, then decreased temperature to room temperature and shut down stirring for several hours. Clear crystals form in aqueous layer; organic layer contains yellowish needles and "blobby" cauliflower-like crystals. Increased temperature to 120° C. and at 60° C. all needles dissolved in organic layer. But "blobby" crystals still present which indicates that NHPI is more soluble in 2-butanol than phthalic anhydride. All crystals in aqueous layer dissolved as well. Separated organic and aqueous phase at 120° C. and let cool to room temperature. Formation of clear crystals in aqueous and yellow precipitate in organic phase. Filtered crystals and dried at 4 hours at 50° C. in N2 ventilated oven.

Filtration of organic layer yielded 840 mg precipitate (24% NHPI, 65% phthalic acid, 11% ester).

Filtration of aqueous layer yielded 2.58 grams precipitate (no organic compound).

The NHPI product fractions in all examples were characterized by 13C NMR.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing N-substituted cyclic imide compounds comprising the steps of:

a. contacting a cyclic carboxylic acid anhydride with a hydroxylamine or a salt thereof in an aqueous solution to form a first mixture wherein the pH of the first mixture is from about 2 to about 6 and wherein the molar ratio of hydroxylamine to carboxylic acid anhydride in the first mixture is from about 0.8 to about 2.0 prior to reaction;

b. allowing the mixture to undergo reaction such that a N-substituted cyclic imide compound is formed;

c. adding an acid to the first mixture to lower the pH of the first mixture to form a second mixture; and d. removing at least a portion of the N-substituted cyclic imide compound from the second mixture;

wherein at least a portion of the N-substituted cyclic imide compound is removed from the first mixture prior to addition of the acid.

2. The process of claim 1, further comprising the steps of:

a. adding an acid to the second mixture to lower the pH of the second mixture; and b. removing at least a portion of the N-substituted cyclic imide compound.

3. The process of claim 1, wherein the N-substituted cyclic imide compound obeys the general formula:

(III)

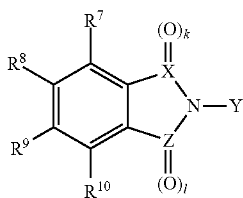

wherein each of $R^7$, $R^8$, $R^9$, and $R^{10}$ is independently selected from hydrocarbyl and substituted hydrocarbyl radicals having 1 to 20 carbon atoms, or the groups $SO_3H$, $NH_2$, OH and $NO_2$, or the atoms H, F, Cl, Br and I; each of X and Z is independently selected from C, S, $CH_2$, N, P and elements of Group 4 of the Periodic Table; Y is O or OH; k is 0, 1, or 2, and 1 is 0, 1, or 2.

4. The process of claim 1, wherein the N-substituted cyclic imide compound is N-hydroxyphthalimide.

5. The process of claim 1, wherein the carboxylic acid anhydride is phthalic anhydride.

6. The process of claim 1, wherein the carboxylic acid anhydride is a substituted phthalic anhydride.

7. The process of claim 1, wherein the hydroxylamine is derived from the group consisting of hydroxylamine sulfate and hydroxylamine hydrochloride.

8. The process of claim 1, wherein the hydroxylamine salt is contacted with a deprotonating base to convert at least a portion of the hydroxylamine salt to a deprotonated hydroxylamine to form a hydroxylamine mixture prior to said contacting (a).

9. The process of claim 8, wherein the hydroxylamine mixture has a pH of from about 6 to about 8.

10. The process of claim 1, wherein the pH of the first mixture is from about 4 to about 6.

11. The process of claim 1, wherein the pH of the second mixture is from about 1 to about 3.

12. The process of claim 1, wherein the pH of the second mixture is from about 1 to about 2.

13. The process of claim 1, wherein at least a portion of the reaction occurs at a temperature of less than about 100° C.

14. The process of claim 1, wherein at least a portion of the reaction occurs at a temperature of less than about 90° C.

15. The process of claim 1, wherein the molar ratio of hydroxylamine to carboxylic acid anhydride in the first mixture is from about 1 to about 1.8 prior to reaction.

16. The process of claim 1, wherein the molar ratio of hydroxylamine to carboxylic acid anhydride in the first mixture is from about 1 to about 1.5 prior to reaction.

17. The process of claim 1, wherein the molar ratio of hydroxylamine to carboxylic acid anhydride in the first mixture is from about 1.1 to about 1.4 prior to reaction.

18. The process of claim 1, wherein the molar ratio of hydroxylamine to carboxylic acid anhydride in the first mixture is from about 1.2 to about 1.3 prior to reaction.

19. A process for producing N-hydroxyphthalimide comprising the steps of:

a. contacting a hydroxylamine salt with a deprotonating base to convert at least a portion of the hydroxylamine salt to a deprotonated hydroxylamine to form a hydroxylamine mixture wherein the pH of the hydroxylamine mixture is from about 6 to about 8;

b. contacting the deprotonated hydroxylamine with phthalic anhydride at a molar ratio of the hydroxylamine to the pthalic anhydride from about 1 to about 1.5 to form a first mixture wherein the first mixture has a pH of from about 4 to about 6;

c. allowing the mixture to undergo reaction such that N-hydroxylphthalimide is formed wherein at least a portion of the reaction occurs at a temperature of less than about 100° C.;

c1. removing at least a portion of the N-hydroxylphthalimide from the first mixture;

d. adding an acid to the first mixture to lower the pH of the first mixture to form a second mixture wherein the second mixture has a pH of from about 1 to about 3; and e. removing at least a portion of the N-substituted phthalimide compound from the second mixture.

* * * * *